(12) United States Patent
Lin Lee (10) Patent No.: US 7,674,241 B2
(45) Date of Patent: Mar. 9, 2010

(54) SAFE MEDICAL-DRUG INJECTOR AND COLLAPSIBLE PLUNGER COMBINATION THEREOF

(75) Inventor: Lee Lin Lee, Taipei (TW)

(73) Assignee: Bencha International Group Inc., Taipei (TW)

( * ) Notice: Subject to any disclaimer, the term of this patent is extended or adjusted under 35 U.S.C. 154(b) by 467 days.

(21) Appl. No.: 11/600,755

(22) Filed: Nov. 17, 2006

(65) Prior Publication Data

US 2007/0185458 A1    Aug. 9, 2007

(30) Foreign Application Priority Data

Jan. 27, 2006   (TW) ............... 95103637 A
Mar. 20, 2006   (TW) ............... 95109467 A (51) Int. Cl.
*A61M 5/00* (2006.01)

(52) U.S. Cl. ...................... 604/111; 604/110

(58) Field of Classification Search ............... 604/110, 604/111, 229
See application file for complete search history.

(56) References Cited

U.S. PATENT DOCUMENTS

| | | | |
|---|---|---|---|
| 4,394,863 A | 7/1983 | Bartner | |
| 4,425,120 A | 1/1984 | Sampson et al. | |
| 5,049,133 A | 9/1991 | Villen Pascual | |
| 5,053,010 A | 10/1991 | McGary et al. | |
| 5,084,018 A | 1/1992 | Tsao | |
| 5,114,410 A | 5/1992 | Caralt Batlle | |
| 5,180,369 A | 1/1993 | Dysarz | |
| 5,405,362 A | 4/1995 | Kramer et al. | |
| 5,613,952 A | 3/1997 | Pressly, Sr. et al. | |
| 5,795,336 A | 8/1998 | Romano et al. | |
| 5,928,188 A * | 7/1999 | McGary et al. | ............ 604/506 |
| 5,984,899 A | 11/1999 | D'Alessio et al. | |
| 5,993,470 A | 11/1999 | Yoon | |
| 6,010,486 A | 1/2000 | Carter et al. | |
| 6,015,396 A | 1/2000 | Buttgen et al. | |
| 6,036,674 A | 3/2000 | Caizza et al. | |
| 6,099,500 A | 8/2000 | Dysarz | |
| 6,221,052 B1 | 4/2001 | Caizza et al. | |

(Continued)

FOREIGN PATENT DOCUMENTS

CN     2678668 Y     2/2005

(Continued)

*Primary Examiner*—Nicholas D Lucchesi
*Assistant Examiner*—Gerald Landry, II
(74) *Attorney, Agent, or Firm*—Ming Chow; Sinorica, LLC (57) ABSTRACT

A safe medical-drug injector with a collapsable plunger combination thereof is proposed. The injector includes a hub connected with a needle, a hollow barrel, and a collapsable plunger combination including a hollow cannula and a retractable plunger that is telescoped with the hollow cannula. At least a stress adjustable notch is formed at the core of the retractable plunger or in an upper edge of the hollow cannula, and at least one raised portion is formed on an outer lateral side of the retractable plunger near the stress adjustable notch to be correspondingly embedded with at least a depression formed on an inner lateral side of the hollow cannula. The engagement between the raised portion and the depression is released to make the retractable plunger drawn back to the hollow cannula when a following press is applied on the hollow cannula after the safe medical-drug injector completes an injection.

14 Claims, 9 Drawing Sheets

U.S. PATENT DOCUMENTS

| | | |
|---|---|---|
| 6,228,054 B1 | 5/2001 | Dysarz |
| 6,368,303 B1 | 4/2002 | Caizza |
| 6,393,898 B1 * | 5/2002 | Hajduk et al. ............... 73/54.05 |
| 6,517,516 B1 | 2/2003 | Caizza |
| 6,569,123 B2 | 5/2003 | Alchas et al. |
| 6,585,690 B1 * | 7/2003 | Hoeck et al. ................. 604/110 |
| 6,592,555 B1 | 7/2003 | Wen-Pi et al. |
| 6,632,198 B2 | 10/2003 | Caizza |
| 6,712,787 B1 | 3/2004 | Dysarz |
| 6,752,782 B2 | 6/2004 | Liao |
| 6,840,291 B2 | 1/2005 | Caizza et al. |
| 6,872,193 B2 * | 3/2005 | Shaw et al. ............ 604/164.07 |
| 6,945,960 B2 | 9/2005 | Barker et al. |
| 6,966,898 B1 * | 11/2005 | Pouget et al. ................ 604/197 |
| 6,994,690 B2 | 2/2006 | Kichne |
| 7,014,622 B1 | 3/2006 | Pressly, Sr. et al. |
| 7,258,678 B2 * | 8/2007 | Wilkinson ................... 604/110 |
| 2003/0045838 A1 * | 3/2003 | Woodard et al. ............. 604/218 |
| 2005/0131350 A1 * | 6/2005 | Shaw et al. ............ 604/168.01 |
| 2008/0097308 A1 * | 4/2008 | Schiller et al. .............. 604/110 |

FOREIGN PATENT DOCUMENTS

| | | |
|---|---|---|
| TW | 0520995 | 4/2001 |

* cited by examiner

SAFE MEDICAL-DRUG INJECTOR AND COLLAPSIBLE PLUNGER COMBINATION THEREOF

BACKGROUND OF THE INVENTION

1. Field of the Invention

The present invention relates to a safe medical-drug injector and, more particularly, to an automatically retractable safe medical-drug injector and a collapsible plunger combination thereof. The collapsible plunger enables the users of the injector to manipulate the injector by single-hand.

2. Description of the Related Art

It is well known that the major route of infection to the diseases such as Acquired Immune Deficiency Symptom (AIDS), hepatitis B or C is blood transportation. For the requirement to avoid the risk of such infection, an injector used by medical personnel or medicine taker is generally designed to be an unreusable or disposable syringe which can be used for only one time. However, most kinds of disposable syringes are not convenient to manipulate for that the user have to perform the injection by two hands. Accordingly, a diabetic may still choose to use the conventional injector instead of the disposable syringe to take insulin, and therefore the risk of getting infected with diseases through blood transportation still remains.

Figure 1A:
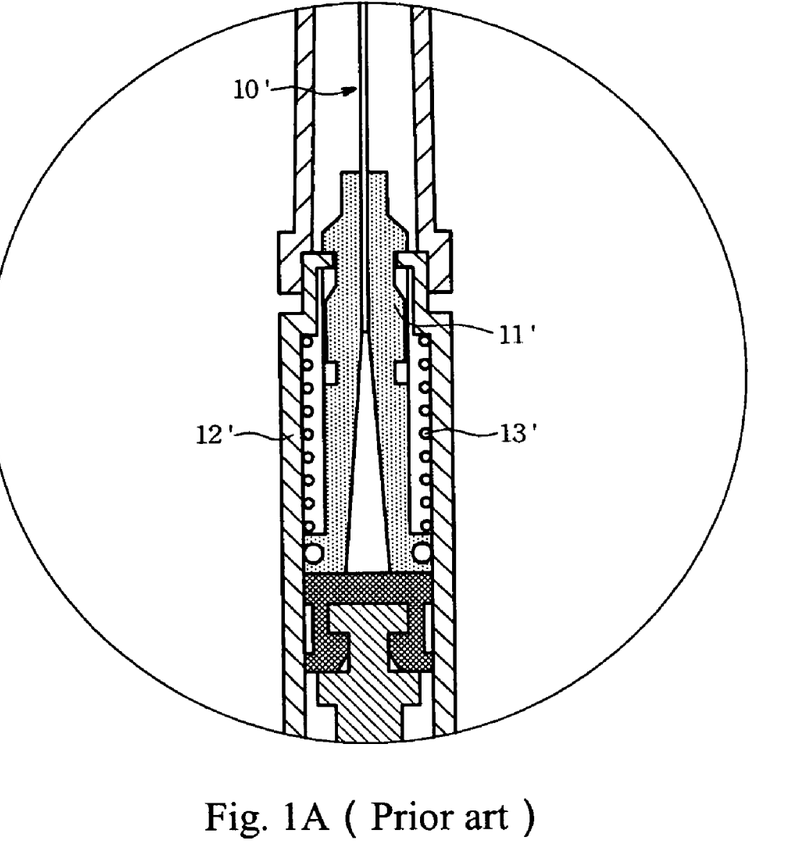
FIGS. 1A and 1B are cross sectional view of a conventional automatically retractable safe injector with breakable portion.
Figure 1B:
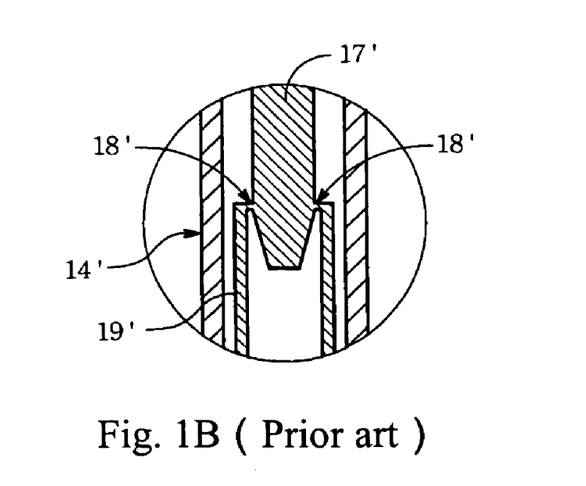

In view of this, a novel safe medical-drug injector which can be manipulated by single-hand is proposed and disclosed in Taiwan patent No. 520995 and U.S. Pat. No. 6,712,793. As shown in FIGS. 1A and 1B, the disclosed syringe includes a hollow barrel 12', a needle hub 11' for accommodating a needle 10', an annular retracting spring 13' and a breakable inward plunger 14'. The breakable inward plunger 14' further includes a proximal part 17', a breakable portion 18' and a hollow distal part 19' that are one-piece formed. When an injection is performed and completed, the user is able to break the breakable portion 18' of the plunger 14', which is inserted into the hollow barrel 12', by further pressing on the plunger 14' and cause the proximal part 17' to draw into the hollow distal part while cause the needle hub 11' and the used needle 10' together to draw into the hollow barrel 12'.

As far as the plunger 14' is concerned, the high symmetry and the high precision in making the breakable portion 18' are required for the consideration of the operational convenience when the force is applied on the plunger 14'. Therefore, the manufacturing of the plunger 14' is always costly due to the critical dimensional tolerance for the mold used to one-piece mold the plunger 14'. Besides, the break of the breakable portion 18' and the retraction of the needle hub 11' are not always achieved unless the direction of the applied force of the injection is limited to substantially parallel to the longitudinal axis of the plunger 14'. As a result, it is hard to perform an injection on the organ with larger curvature such as the back of neck, ear, eye, etc.

BRIEF SUMMARY OF THE INVENTION

The object of the present invention is to provide a safe medical-drug injector and a collapsible plunger combination thereof for the user to complete an injection by single-hand without considering too much about the applied angle of injection.

Another object of the present invention is to provide a safe medical-drug injector and the collapsible plunger combination thereof, wherein the injector is not easily damaged during the assembly and thereby improve the product yield and reduce the manufacturing cost.

Another further object of the present invention is to provide an easily injection-molded safe medical-drug injector and the collapsible plunger combination thereof without considering high precision for the plunger combination so that the dimensional tolerance of manufacturing has a generally reasonable range and the manufacturing cost can be lowered.

Another further object of the present invention is to provide a safe medical-drug injector and the included collapsible plunger combination which is able to absorb the applied force, to resist against lateral shear force, and thereby to improve the convenience of injection and reduce the failure of injection.

Another further object of the present invention is to provide a safe medical-drug injector and the included collapsible plunger combination which enables the increase of the product yield according to a batch molding.

Another further object of the invention is to provide a safe medical-drug injector and the included collapsible plunger combination which is easy to manipulate and make the used needle automatically retracted.

According to the above mentioned objects of the invention, a single-used automatically retractable safe medical-drug injector for injecting liquid medical-drug into human body and the plunger combination of the injector are disclosed.

The safe medical-drug injector comprises a needle hub connecting a needle; a hollow barrel connected with the needle hub for guiding the needle hub to be drawn back to the hollow barrel after an injection is completed; and a collapsable plunger combination inserted into the hollow barrel. The collapsable plunger combination comprises a hollow cannula and a retractable plunger. The hollow cannula comprises a first telescoping part and the retractable plunger comprises a second telescoping part. Especially, there is at least one raised portion formed on the outside wall of the second telescoping part to be correspondingly embedded in at least one depression formed on the inside watt of the first telescoping part. In addition, the hollow cannula is formed with at least one stress adjustable notch on the upper edge and the engagement between the raised portion and the depression is released to make the retractable plunger drawn back to the hollow cannula when the stress adjustable notch deforms due to a following press on the hollow cannula after an injection is completed. As a result, some space of the hollow barrel is spared for accommodating the needle hub.

The disclosed safe medical-drug injector is also designed to provide the retractable plunger and the hollow cannula of the collapsible plunger with improved strength for facilitating the manipulation of the injector by single-hand without limiting the angle of injection.

As described for the disclosed safe medical-drug injector and the plunger combination thereof according to the following second embodiment, the hollow cannula is formed with at least one exhausting hole on the sidewall far away from the first telescoping part retractable plunger to reduce the air resistance at the moment when the retractable plunger is drawn back to the hollow cannula. Thereby, the convenient of manipulating the injector can be further improved.

According to the third and forth embodiments, the raised portion comprises a plurality of adjacent rows of transversely convex annular ribs or a plurality of spaced rows of transversely convex annular ribs. Correspondingly, the depressions on the hollow cannula are selected from the group consisting of groove and cavity or the group consisting of a plurality of adjacent rows of transversely concave annular ribs and a plurality of spaced rows of transversely concave annular ribs.

Furthermore, as described according to the fifth embodiment, there is a stopper set adjacent to the hollow barrel for preventing the needle hub from escaping and guiding the needle hub to retract after an injection is completed. Alternatively, the outside wall of the retractable plunger is formed with rough region above the raised portion according to the sixth embodiment.

In addition, as described according to the seventh embodiment, the safe medical-drug injector is designed that the hollow barrel connected with the needle hub is one-piece formed with a narrow barrel having its diameter smaller than that of the hollow barrel near the needle hub and there is a block set adjacent to the opening of the narrow barrel for preventing the needle hub from escaping and guiding the needle hub to retract after an injection is completed.

Also, according to the eighth embodiment, the block is a neck portion one-piece injection-molded on the hollow barrel to ensure that the best retraction distance is under controlled.

Being different from the prior one-piece formed breakable connection of the plunger, the disclosed safe medical-drug injector and the collapsable plunger combination thereof are designed to be separate elements before assembled, and thereby the impact or hurt on the whole injector can be avoided. Two-piece plunger can be manufactured without high precision considered for the prior one-piece plunger, and this towers the manufacturing cost and gives the tolerance for the product quality a more reasonable range.

Especially, the capability of resisting against lateral shear force make the disclosed two-piece plunger have greater force equilibrium feature than the prior art. Therefore, a medical personnel or medicine taker can perform an injection themselves by single hand without limiting the angle of injection to a particular orientation.

DETAILED DESCRIPTION OF THE INVENTION

Reference will now be made to the drawings in which the various elements of the present invention will be given numerical designations and in which the invention will be discussed so as to enable one skilled in the art to make and use the invention.

Figure 2:
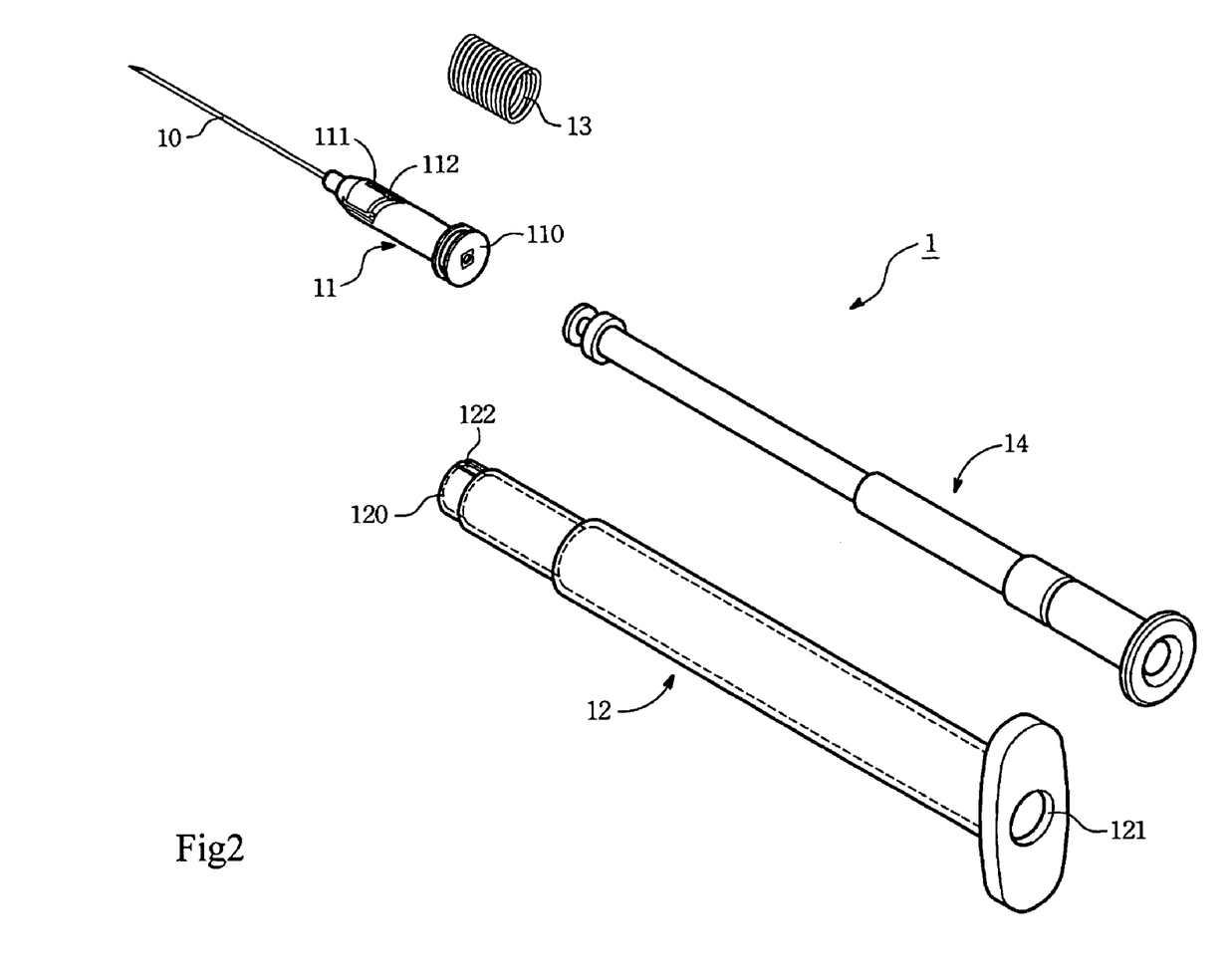
FIG. 2 is an exploded schematic view of the safe medical-drug injector and the collapsible plunger combination thereof according to the first embodiment of the invention.
Figure 3:
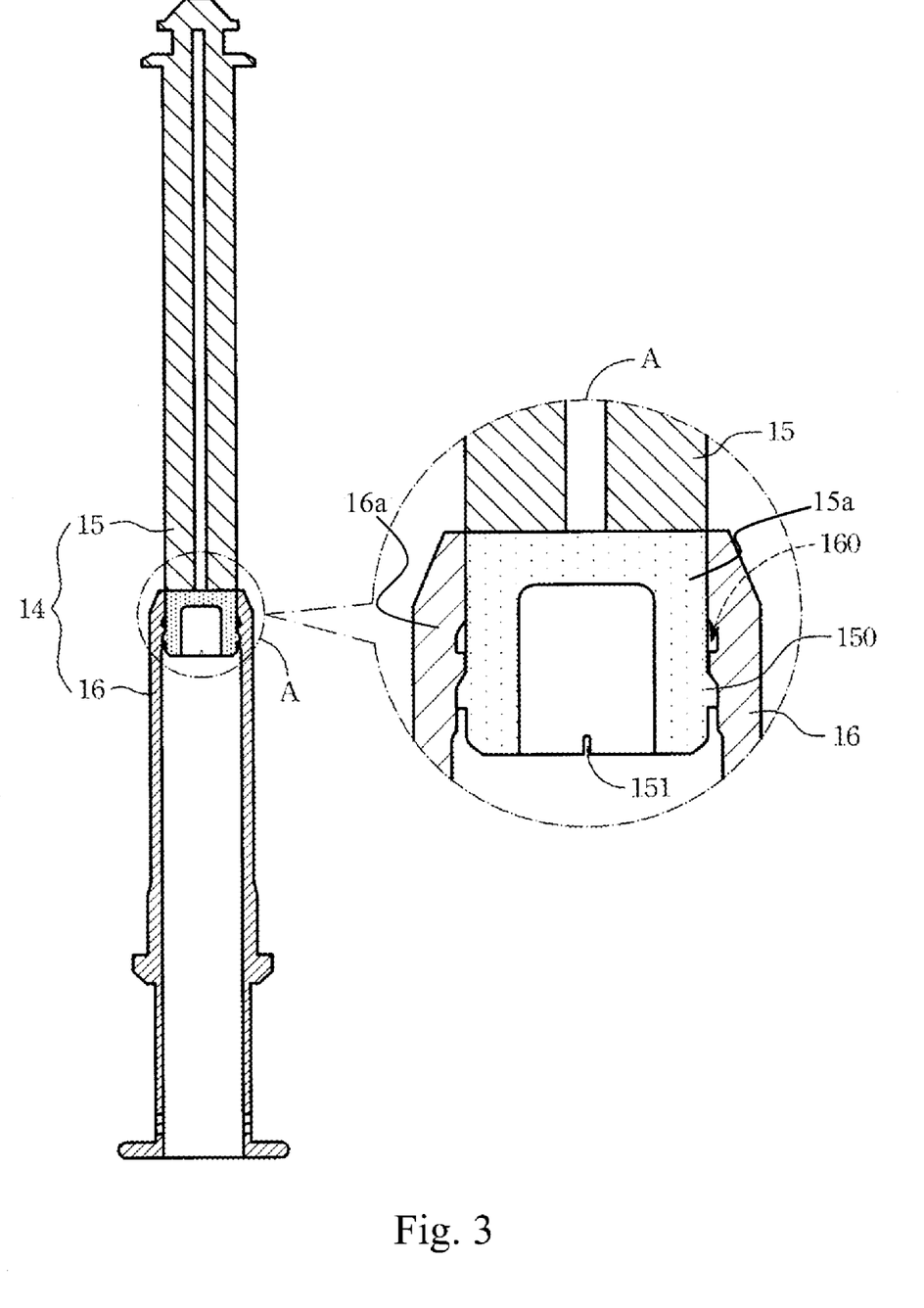
FIG. 3 is a cross sectional view with enlarged view of the safe medical-drug injector according to the first embodiment.
Figure 4:
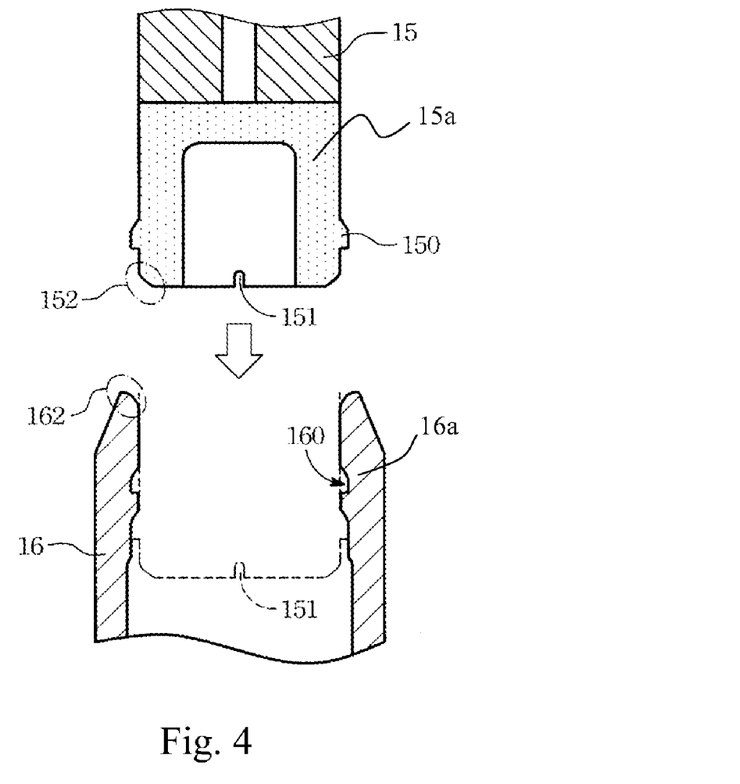
FIG. 4 is a schematic view illustrating how the retractable plunger and the hollow cannula of the safe medical-drug injector are connected according to the first embodiment.

As shown in FIGS. 2, 3 and 4, the automatically retractable safe medical-drug injector and the collapsible plunger combination thereof for injecting liquid medical-drug into human bodies by single-hand are illustrated by perspective view and cross sectional view. It is noted that the drawings here are simplified to schematically illustrate the preferred embodiments of the present invention, and the elements referred to and the number, shape, dimension and scale thereof are not limited to these embodiments.

Referring to FIG. 2, the automatically retractable safe medical-drug injector 1 includes at least a needle hub connecting a needle 11, a hollow barrel 12 and a collapsible plunger combination 14 that is inserted into the hollow barrel 12. The hollow barrel 12 is connected with the needle hub 11 to guide the after-used needle 11 drawn back by means of an annular retracting spring 13. In addition, the hollow barrel 12 has a front end 120 and a rear end 121.

Specifically, the needle 10 passes one end of the needle hub 11 and penetrates the center of the needle hub 11 while a disc 110 is provided on the other end of the needle hub 11 for supporting the compressed annular retracting spring 13. A plurality of positioning grooves 111 used to fastened with the front end 120 of the hollow barrel 12 and a U-shaped slide passage 112 connected to the positioning grooves 111 are set between two ends of the needle hub 11. The needle hub 11 moves along the U-shaped slide passage 112 to retract toward a direction opposite to the injection direction when the compressed annular retracting spring 13 is released to nature, and the U-shaped slide passage 112 can be used to control the retract distance of the needle hub 11 to avoid exposing the needle 10 out. It should be noted that any other equivalent elastic elements able to be compressed and released to nature such as folded metal sheets can be taken to replace the annular retracting spring 13.

The hollow barrel 12 is provided with a plurality of elastic retaining hooks 122 that face the center of the hollow barrel 12 at the front end. The needle hub 11 is firmly fastened with the hollow barrel 12 via the positioning grooves 111 and the retaining hooks 122, and retracts back to the hollow barrel 12 when the fastening is released by the press on the injector to make the retaining hooks 122 elastically expand after the injection is completed.

Referring to FIG. 3, the automatically retractable safe medical-drug injector 1 according to first embodiment is mainly characterized in the design of the collapsable plunger combination 14. As shown, the collapsable plunger combination 14 is two-piece configuration and comprises retractable plunger 15 and hollow cannula 16, which are manufactured by injection molding individually. The hollow cannula 16 comprises a first telescoping part 16a and the retractable plunger 15 comprises a second telescoping part 15a. The first telescoping part telescopes with the second telescoping part. A plurality of raised portions 150 are formed on the outside wall of the second telescoping part 15a of the retractable plunger 15 while a plurality of depressions 160 are formed on the inside wall of the first telescoping part 16a of the hollow cannula 16 to be correspondingly embedded with the raised portions 150. The raised portions 150 and the depressions 160 engage to each other until the press on the injector after the injection is completed releases the engagements. As a result, the retractable plunger 15 can be drawn back to the hollow cannula 16, and thereby spare space of the hollow barrel 12 for accommodating the needle hub (not shown).

Herein, the retractable plunger 15 or the hollow cannula 16 is manufactured by injection-molding the elastic material selected form group consisting of Polyethylene (PE), polyvinyl chloride (PVC), and rubber or the elastic material selected from group consisting of Polypropylene (PP) and AN series transparent ebonite. The main part of the retractable plunger 15 can be shaped to be cross ribs or column pipes.

Furthermore, the retractable plunger 15 is provided with at least one lateral stress adjustable notch 151 at the core of the second telescoping part (as shown in region A of FIG. 3) to keep the plunger in stress equilibrium. The stress adjustable notch 151 is a cavity, a blind hole or a through hole for example. In addition, the lateral stress adjustable notches 151 are positioned near but not reach the raised portions 150. Therefore, the lateral stress adjustable notches 151 deform when a following press on the hollow cannula is applied after the injection is completed and the deformation releases the engagements between the raised portions 150 and the depressions 160.

The mentioned raised portions 150 can be outward protruding dots one-piece formed on the outside wall of the retractable plunger 15. The shape, size, numbers, and arrangement of the dots are not limited but illustrated here with six numbers for exemplification. Also, the illustrated convex annular ribs are one of the equivalents of the raised portions 150.

FIG. 4 shows the structure of the hollow cannula 16. For the purpose of firmly connecting the retractable plunger 15 with the hollow cannula 16, the hollow cannula 16 is formed with a plurality of depressions 160 on the inside wall of the first telescoping part 16a of the cannula 16 to be correspondingly embedded with the raised portions 150 on the second telescoping part 15a. These depressions 160 can be grooves, cavities, or partial or complete concave annular ribs, and the cross section of the depressions 160 can be C-shaped, fillet-shaped or irregular-shaped. All modifications of the depressions 160 designed to be correspondingly engaged with the raised portions 150 of the retractable plunger 15 are covered as the equivalents of the depressions 160 according to the present embodiment. It should be noted that the complete concave annular ribs are considered as the preferred aspect for the depressions 160 to avoid that the retractable plunger 15 can not be rotated due to the improper position of the raised portions 150 in assembling.

As shown in FIG. 4, a further investigation is taken on the second telescoping part 15a of the retractable plunger 15 and the first telescoping part 16a of the hollow cannula 16 of the collapsable plunger combination 14. The tower edge 152 of the raised portions 150 for the retractable plunger 15 is designed to be fillet edge, and the upper edge 162 on the inner side of the hollow cannula 16 has a shape selected from the group consisting of arc, fillet and inline so that the inner diameter of the opening at the upper edge 162 of the hollow cannula 16 is somewhat larger than the diameter of the retractable plunger 15 at the tower edge. In this way, the retractable plunger 15 can be drawn into the hollow cannula 16 when the injection is completed and the engagement is released.

Figure 5:
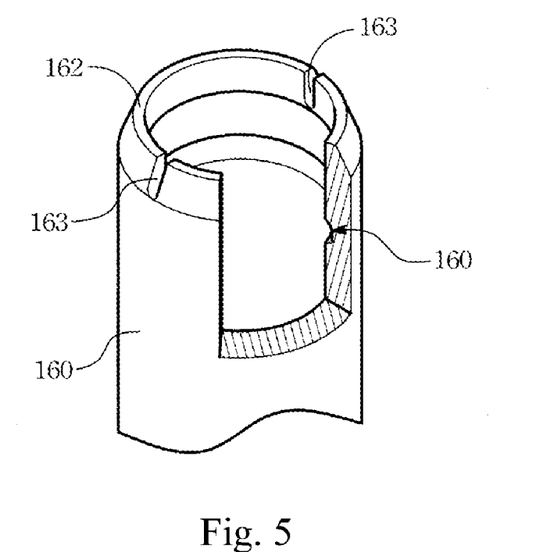
FIG. 5 is a schematic view showing the hollow cannula of the safe medical-drug injector according to the first embodiment of the invention.

Since the retraction force of the retractable plunger 15 and the tensile strength of the hollow cannula 16 is requested to reach the mechanical test standard during the manufacturing of the collapsible plunger combination 14. Therefore, as shown in FIG. 5, the inclined upper edge 162 of the hollow cannula 16 is further formed with at least one stress adjustable notch 163 positioned near but not reach the depressions 160 on the inner side of the hollow cannula 16. According to the embodiment, the adjustable notch 163 can be cavity or blind hole.

The retractable plunger and the hollow cannula of the collapsible plunger combination according to the safe medical-drug injector of the present invention are strengthened to satisfy various possibilities of manipulation of single-hand.

FIGS. 6 to 13 illustrate various embodiments for the safe medical-drug injector and the collapsible plunger combination thereof according to the present invention. It is to be noted that the following second to eighth embodiments are explained with the characteristics that are different from that of the first embodiment and the characteristics that are same as that of the first embodiment are omitted.

Figure 6:
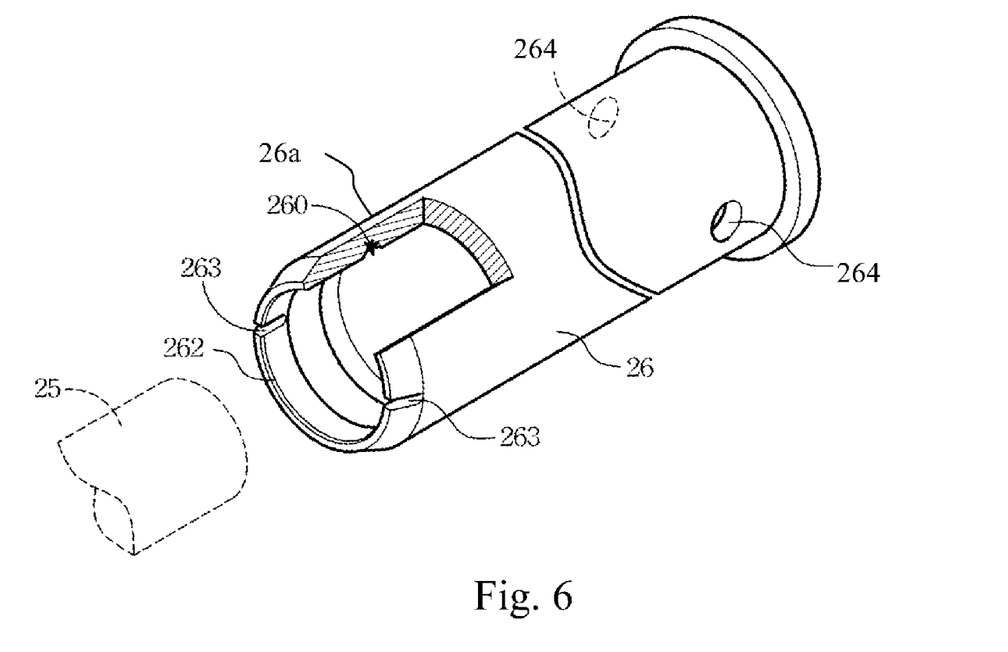
FIG. 6 is an exploded cross sectional view showing the safe medical-drug injector according to the second embodiment of the invention.

FIG. 6 illustrates the safe medical-drug injector and the collapsable plunger combination according to the second embodiment. As shown in the figure, the hollow cannula 26 is formed with at least one exhausting hole 264 on the sidewall far away from the first telescoping part 26a (as shown in region A in FIG. 3). By means of the exhausting hole 264, the retractable plunger 25 can smoothty retract back to the hollow cannula 26 for that the air resistance is unloaded and thereby facilitates the manipulation of the injector. The concave annular ribs 260 is used to replace the depressions 160 in the first embodiment white the upper edge 262 and the stress adjustable notch 263 are the same as that in the first embodiment.

Figure 7:
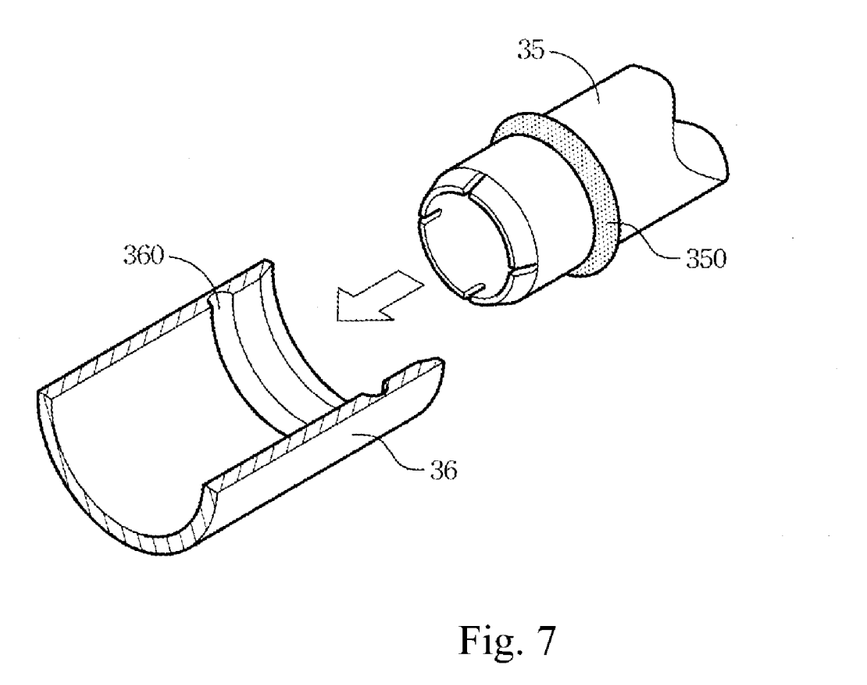
FIG. 7 is a perspective view showing the cross section of the collapsible plunger combination of the safe medical-drug injector according to the third embodiment of the invention.

According to the safe medical-drug injector in the third embodiment, as shown in FIG. 7, at least one transversely convex annular rib 350 with their profile being continuous or discontinuous are formed on the outside of the retractable 35 for replacing the raised portions 150 in the first embodiment. Correspondingly, at least one transversely concave annular rib 360 or annular groove with their profile being continuous or discontinuous are formed on the inside of the hollow cannula 36 for replacing the depressions 160 in the first embodiment. The convex annular rib 350 and the concave annular rib 360 are arranged to be in single-line or in multi-line such as shown in the FIG. 8 according to the safe medical-drug injector of the fourth embodiment.

Figure 8:
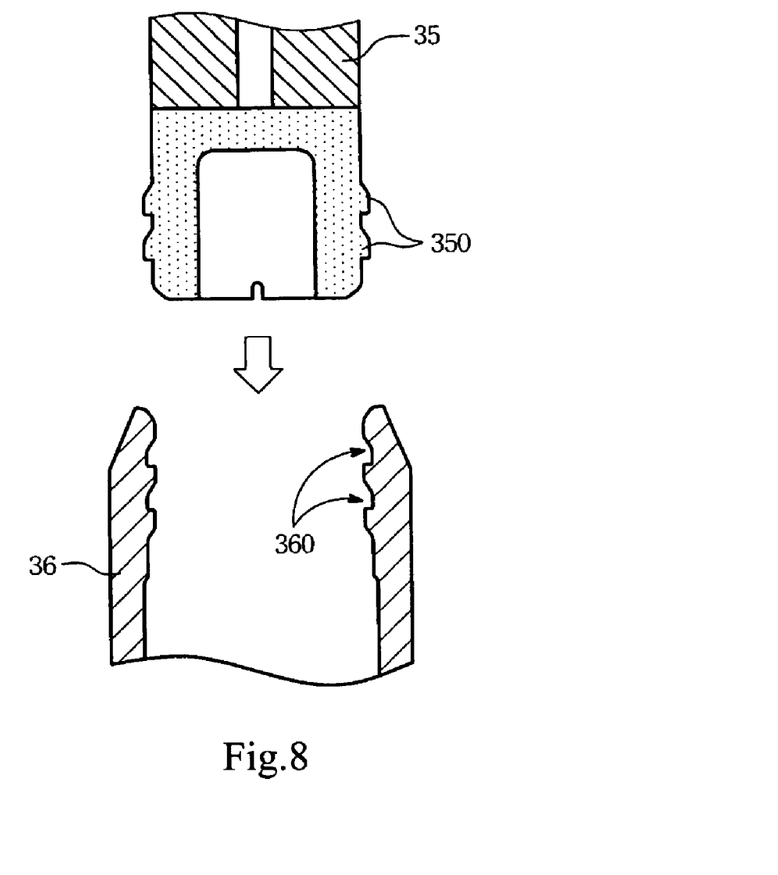
FIG. 8 is a cross sectional view showing the collapsible plunger combination of the safe medical-drug injector according to the fourth embodiment of the invention.

According to the collapsible plunger combination of the forth embodiment, as shown in FIG. 8, a plurality of spaced rows of transversely convex annular ribs or a plurality of adjacent rows of transversely convex annular ribs 450 with their profile being continuous or discontinuous are formed on the outside of the retractable plunger 45 for replacing the raised portions 150 in the first embodiment. Correspondingly, a plurality of spaced or adjacent rows of transversely concave annular ribs or annular grooves 460 with their profile being continuous or discontinuous are formed on the inside of the hollow cannula 46 for replacing the depressions 160 in the first embodiment.

Figure 9:
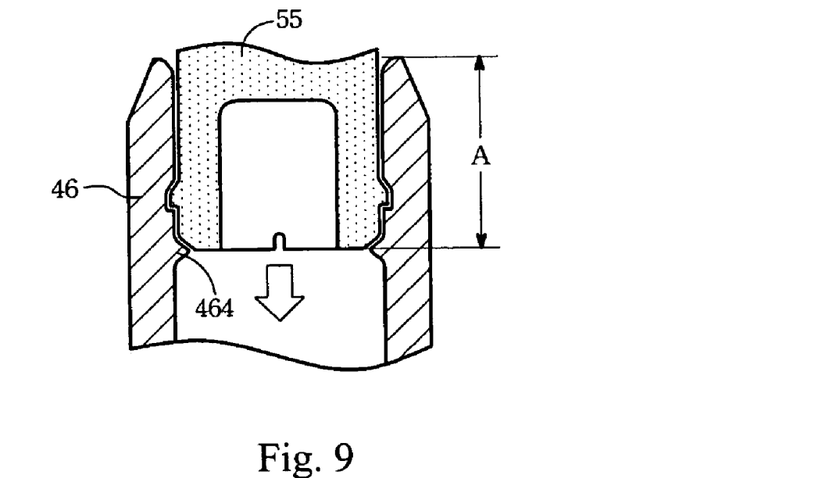
FIG. 9 is a cross sectional view showing the collapsible plunger combination of the safe medical-drug injector according to the fifth embodiment of the invention.

On the other hand, according to the fifth embodiment shown in FIG. 9, there are a plurality of stoppers 564 formed on the inner sidewall of the hollow cannula 56 near the depressions or the concave annular ribs or the annular grooves 560 at the region A, which is the telescoping part of the retractable plunger 55 and the hollow cannula 56 for stopping the retractable plunger 55 white the injection is performing. These stoppers 564 can be the raised portions one-piece formed on the hollow cannula 56 or the added blocks, and the stoppers 564 each has its extending plane being vertical to the longitudinal axis or inclined in the same direction as the retraction direction of the retractable plunger 55.

Figure 10:
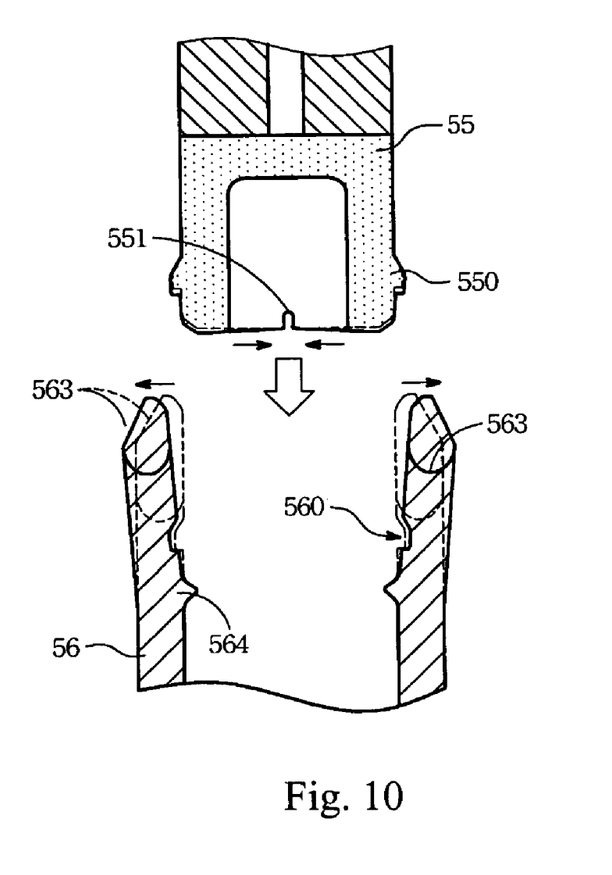
FIG. 10 is a schematic view showing how the retractable plunger of the safe medical-drug injector is drawn back to the hollow cannula according to the fifth embodiment.

In a preferred aspect for the fifth embodiment of the invention, the stoppers 564 are designed to be inclined in the same direction as the retraction direction of the retractable plunger 55. Therefore, as shown in FIG. 10, the stress adjustable notch 551 inwardly deforms to make the raised portions 550 contracted and drawn into the hollow cannula 56 when the user pushes the collapsible plunger combination after the injection is completed. Meanwhile, the downward inclined stoppers 564 guide the retractable plunger 55 to slip in. Especially, the elasticity of the hollow cannula 56 enables the stress adjustable notch 563 on the upper edge of the hollow cannula 56 to instantly transversely expand and thereby facilitates the retraction of the retractable plunger 55 into the hollow cannula 56.

Figure 11:
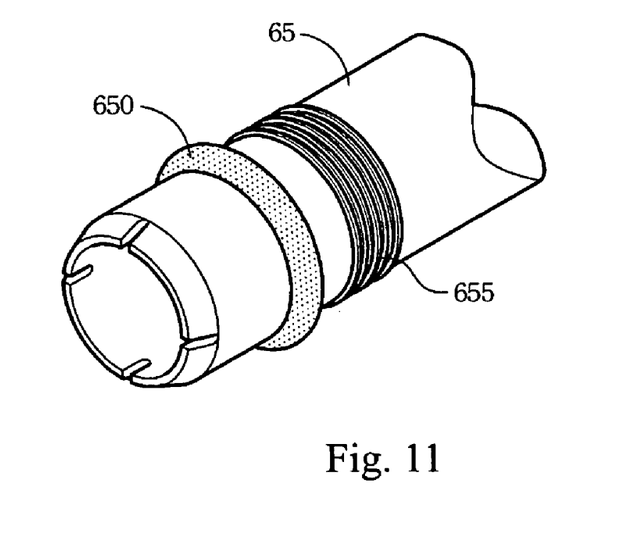
FIG. 11 is a perspective view showing that the retractable plunger of the safe medical-drug injector is provided with rough region according to the sixth embodiment of the invention.

Referring to FIG. 11, the safe medical-drug injector and the collapsible plunger combination thereof according to the sixth embodiment of the invention is formed with rough region 655 on the outer sidewall of the retractable plunger 65 above the raised portions 650. The rough region 655 can be formed by uneven grooves, transverse strips, or granular articles and is used for counteracting the force applied on the plunger to prevent the retractable plunger 65 from retracting into the hollow cannula in advance when the injection is not completed.

The automatically retractable safe medical-drug injector and the collapsable plunger combination thereof are designed to be two-piece, i.e. the retractable plunger and the hollow cannula are separately injection molded before assembling. In this way, the impact or hurt on the whole injector can be reduced. Such plunger can be manufactured without the high precision required for the one-piece plunger, so as to tower the manufacturing cost and the tolerance for the product quality can be improved to be more reasonable.

Especially, the capability of resisting against lateral shear force make the disclosed two-piece plunger have greater force equilibrium feature than the prior art. Therefore, the medical personnel or medicine taker can perform an injection themselves with single hand without limiting the injecting angle to a particular orientation.

Furthermore, the needle hub 71 of the safe medical-drug injector according to the present invention is preferably designed, which will be described in detail in the following seventh and eighth embodiment with the illustration of FIGS. 12 and 13.

Figure 12:
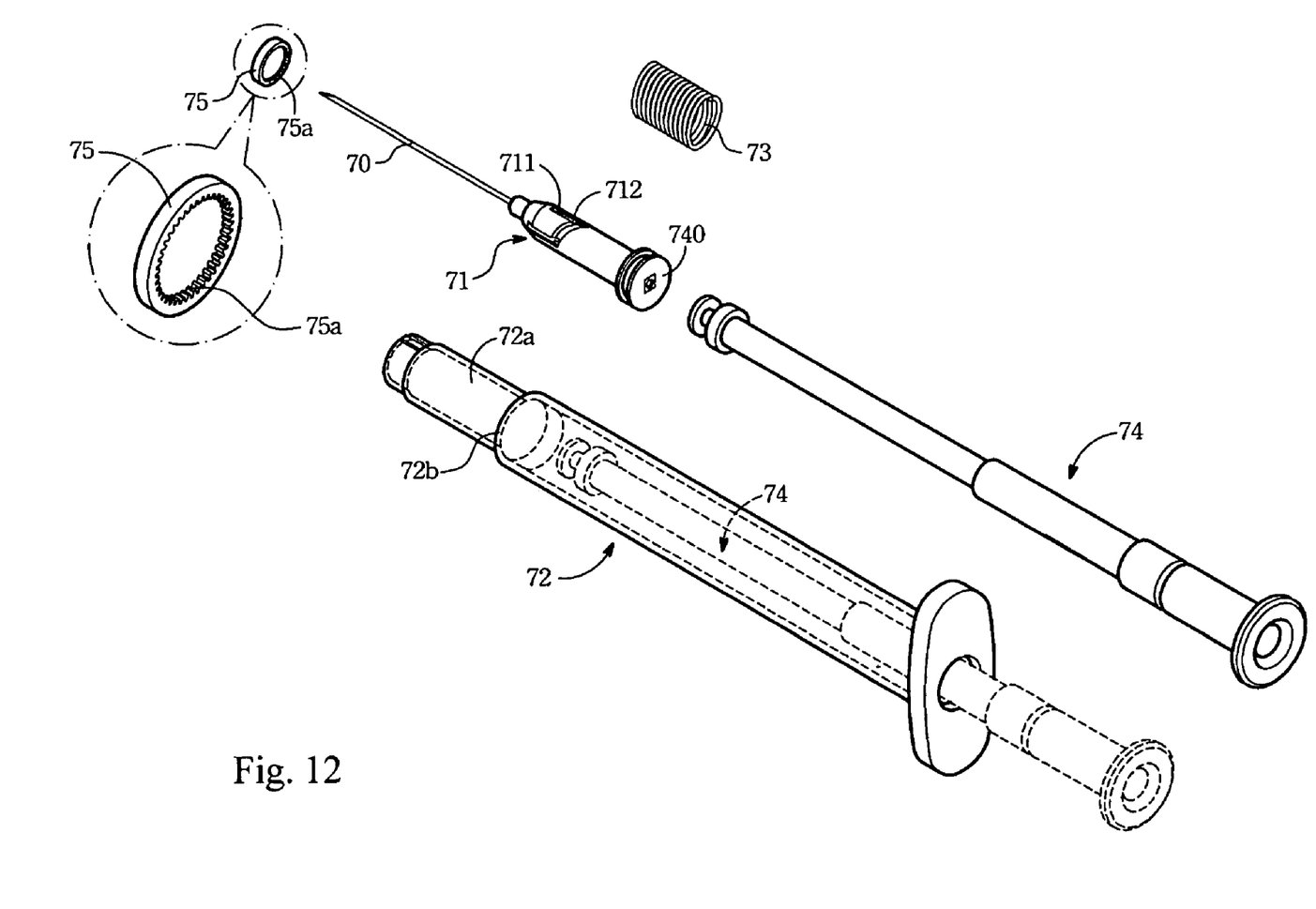
FIG. 12 is an exploded schematic view showing the safe medical-drug injector according to the seventh embodiment of the invention.

As shown in FIG. 12, the collapsible plunger combination 74 of the safe medical-drug injector according to the seventh embodiment has its hollow barrel 72 one-piece formed with a narrow barrel 72a having its diameter smaller than that of the hollow barrel near the needle hub for accommodating the compressed annular retracting spring 73 and the front portion of the needle hub 71 to improve the ability of retracting the needle hub. There is at least a movable or stable stopper 75 set adjacent to the opening 72b of the narrow barrel 72a for preventing the needle hub 71 from escaping and guiding the needle hub 71 to retract after the safe medical-drug injector completes an injection. The movable or stable stopper 75 is formed with through hole 75a in the center for the needle 70 and part of the needle hub 71 to passing through. The through hole 75a of the stopper 75 is smaller than the disc 710 of the needle hub 71 in area to stop the disc 710 and control the needle hub 71 in a preferred retraction position. The stopper can be annular body with its inner sidewall being smooth or regular or irregular. The needle 70, the needle hub 71, the positioning groove 711, the U-shaped slide passage 712 and the annular retracting spring 73 are respectively the same as the needle 10, the needle hub 11, the positioning groove, the U-shaped slide passage 112 and the annular retracting spring 13 in the first embodiment.

Figure 13:
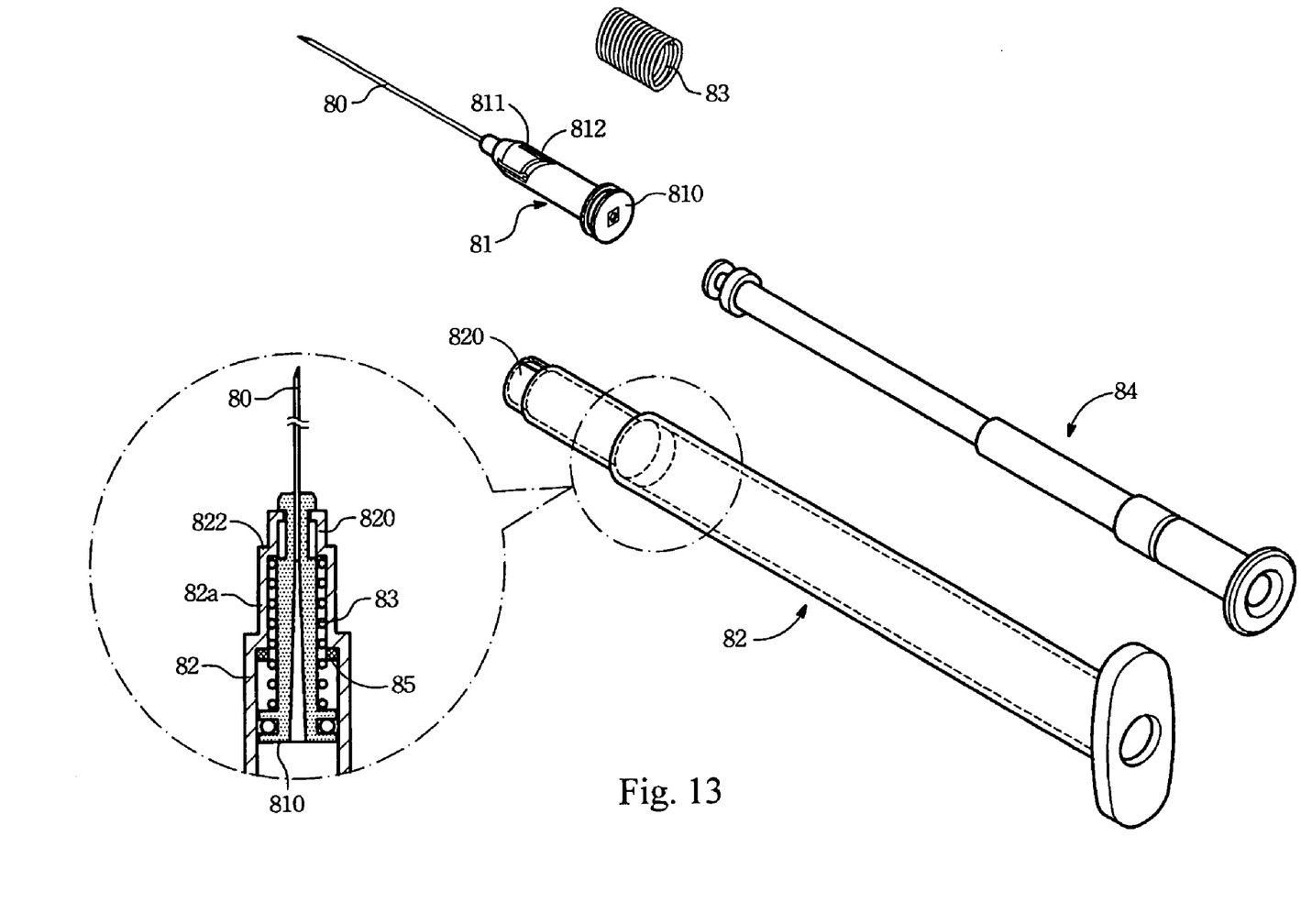
FIG. 13 is an exploded schematic view showing the safe medical-drug injector according to the eighth embodiment of the invention.

Furthermore, as shown in FIG. 13, the eighth embodiment illustrates that there is at least a neck portion 75 one-piece formed on the connect opening of the hollow barrel 82 and the narrow barrel 82a, and the center of the neck portion is formed with through hole having an area smaller than the area of the disc 810. The neck portion 85 can resist the disc 810 and allow the needle 80 and front portion of the needle hub 81 to pass through for preventing the needle hub 71 from escaping and guiding the needle hub 71 to retract after the safe medical-drug injector completes an injection. The collapsible plunger combination 84, the annular retracting spring 83, the positioning groove 811, the U-shaped slide passage 812 and the retaining hook 822 are respectively the same as the collapsible plunger combination 14, the annular retracting spring 13, the positioning groove, the U-shaped slide passage 112 and the retaining hooks 122.

While the invention has been described by way of examples and in terms of the preferred embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A safe medical-drug injector comprising:
a needle hub connecting a needle;
a hollow barrel connected with the needle hub for guiding the needle hub to be drawn back to the hollow barrel after an injection is completed; and
a collapsable plunger combination inserted into the hollow barrel, the collapsable plunger combination comprising a hollow cannula and a retractable plunger, the hollow cannula comprising a first telescoping part and the retractable plunger comprising a second telescoping part, the first telescoping part telescoping with the second telescoping part, there being at least one raised portion formed on an outside wall of the second telescoping part to be correspondingly embedded in at least one depression formed on an inside wall of the first telescoping part, the raised portion and the depression engaging to each other;
wherein the hollow cannula is formed with at least one stress adjustable notch on the upper edge, and wherein the engagement between the raised portion and the depression is released to make the retractable plunger drawn back to the hollow cannula when the stress adjustable notch deforms due to a following press on the hollow cannula after an injection is completed, and thereby spare space of the hollow barrel for accommodating the needle hub.

2. The safe medical-drug injector as set forth in claim 1, wherein the collapsible plunger combination is composed of the hollow cannula and the retractable plunger, and the hollow cannula and the retractable plunger are individually formed by injection molding.

3. The safe medical-drug injector as set forth in claim 1, wherein the raised portion comprises outward protruding dots one-piece formed on the outside wall of the retractable plunger.

4. The safe medical-drug injector as set forth in claim 1, wherein the raised portion comprises a plurality of adjacent rows of transversely convex annular ribs.

5. The safe medical-drug injector as set forth in claim 1, wherein the raised portion comprises a plurality of spaced rows of transversely convex annular ribs.

6. The safe medical-drug injector as set forth in claim 1, wherein the lower edge of the retractable plunger is a fillet edge.

7. The safe medical-drug injector as set forth in claim 1, wherein the outside wall of the retractable plunger is formed with a rough region above the raised portion.

8. The safe medical-drug injector as set forth in claim 1, wherein the upper edge on the inner side of the hollow cannula has a shape selected from the group consisting of arc, fillet and incline.

9. The safe medical-drug injector as set forth in claim 1, wherein the depression is selected from the group consisting of groove and cavity.

10. The safe medical-drug injector as set forth in claim 1, wherein the depression is selected from the group consisting of a plurality of adjacent rows of transversely concave annular ribs and a plurality of spaced rows of transversely concave annular ribs.

11. The safe medical-drug injector as set forth in claim 1, wherein the hollow cannula is formed with at least one exhausting hole on a sidewall far away from the first telescoping part.

12. The safe medical-drug injector as set forth in claim 1, wherein the hollow cannula is formed with a plurality of blocks near the lower part of the depression on the inside wall.

13. A safe medical-drug injector comprising:
a needle hub connecting a needle;
a hollow barrel connected with the needle hub for guiding the needle hub to be drawn back to the hollow barrel after an injection is completed; and
a collapsable plunger combination inserted into the hollow barrel, the collapsable plunger combination comprising a hollow cannula and a retractable plunger, the hollow cannula comprising a first telescoping part and the retractable plunger comprising a second telescoping part, the first telescoping part telescoping with the second telescoping part, there being at least one raised portion formed on an outside wall of the second telescoping part to be correspondingly embedded in at least one depression formed on an inside wall of the first telescoping part, the raised portion and the depression engaging to each other;
wherein the retractable plunger is formed with at least one stress adjustable notch on the core of the first telescoping part, and wherein the engagement between the raised portion and the depression is released to make the retractable plunger drawn back to the hollow cannula when a following press is applied on the hollow cannula after an injection is completed, and thereby spare space of the hollow barrel for accommodating the needle hub.

14. A safe medical-drug injector comprising:
a needle hub connecting a needle;
a hollow barrel connected with the needle hub for guiding the needle hub to be drawn back to the hollow barrel after an injection is completed; and
a collapsable plunger combination inserted into the hollow barrel, the collapsable plunger combination comprising a hollow cannula and a retractable plunger, the hollow cannula comprising a first telescoping part and the retractable plunger comprising a second telescoping part, the first telescoping part telescoping with the second telescoping part, there being at least one raised portion formed on an outside wall of the second telescoping part to be correspondingly embedded in at least one depression formed on an inside wall of the first telescoping part, the raised portion and the depression engaging to each other;
wherein the hollow cannula is formed with at least one stress adjustable notch on the upper edge of the first telescoping part, and wherein the engagement between the raised portion and the depression is released to make the retractable plunger drawn back to the hollow cannula when a following press is applied on the hollow cannula after an injection is completed, and thereby spare space of the hollow barrel for accommodating the needle hub.

* * * * *